United States Patent [19]

Ehrenfreund

[11] Patent Number: 4,766,146
[45] Date of Patent: Aug. 23, 1988

[54] PESTICIDAL SUBSTITUTED HYDRAZINECARBOXYLIC ACID ESTERS

[75] Inventor: Josef Ehrenfreund, Allschwil, Switzerland

[73] Assignee: Ciba-Geigy Corporation, Ardsley, N.Y.

[21] Appl. No.: 25,251

[22] Filed: Mar. 12, 1987

[30] Foreign Application Priority Data

Mar. 20, 1986 [CH] Switzerland ............... 1124/86

[51] Int. Cl.$^4$ ............... A61K 31/34; C07D 307/79
[52] U.S. Cl. ................... 514/469; 549/462
[58] Field of Search ................... 549/462; 514/469

[56] References Cited

U.S. PATENT DOCUMENTS 4,467,104  8/1984  Pilgram et al. ............... 549/462
4,550,121  10/1985  Pilgram et al. ............... 514/469

FOREIGN PATENT DOCUMENTS 048040   3/1982   European Pat. Off. .
067471   12/1982  European Pat. Off. .
0183650  6/1986   European Pat. Off. .
58-222083 12/1983 Japan .
58-222085 12/1983 Japan .
59-222490 12/1984 Japan .

OTHER PUBLICATIONS

Klauke et al, Angew. Chem. 89 pp. 797–804 (1977).
Wood et al, Journal Che. Soc. (1948) pp. 2183–2188.

Primary Examiner—Mary C. Lee
Assistant Examiner—Bernard I. Dentz
Attorney, Agent, or Firm—Kevin T. Mansfield; Edward McC. Roberts

[57] ABSTRACT

The invention relates to novel unsubstituted or substituted 2-fluorocarbonyl-2-(2,3-dihydrobenzofuran-7-yl)hydrazinecarboxylic acid esters of formula

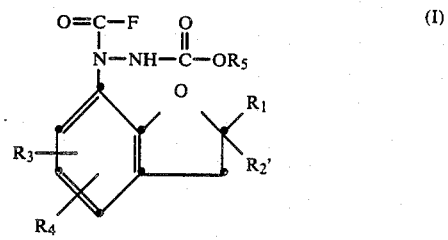

wherein
$R_1$ and $R_2$ are each independently of the other hydrogen or $C_1$-$C_3$alkyl,
$R_3$ and $R_4$ are each independently of the other hydrogen, halogen, $C_1$-$C_4$alkyl or $C_1$-$C_4$-alkoxy, and
$R_5$ is $C_1$-$C_4$alkyl to the preparation of said compounds and to compositions containing them for use in pest control, especially for controlling insects that attack plants and animals. The novel compounds are particularly effective for controlling plant destructive sucking insects.

8 Claims, No Drawings

PESTICIDAL SUBSTITUTED HYDRAZINECARBOXYLIC ACID ESTERS

The present invention relates to novel unsubstituted or substituted esters of 2-fluorocarbonyl-2-(2,3-dihydrobenzofuran-7-yl)hydrazinecarboxylic acid, to their preparation and to the use thereof in pest control.

The novel compounds of this invention have the formula I

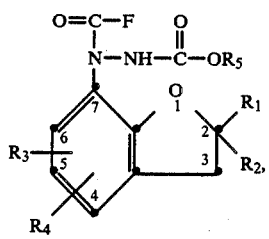

wherein
$R_1$ and $R_2$ are each independently of the other hydrogen or $C_1$–$C_3$alkyl,
$R_3$ and $R_4$ are each independently of the other hydrogen, halogen, $C_1$–$C_4$alkyl or $C_1$–$C_4$-alkoxy, and
$R_5$ is $C_1$–$C_4$alkyl.

Preferred compounds of formula I are those wherein $R_1$, $R_2$, $R_3$ and $R_4$ are each independently hydrogen or methyl and $R_5$ is methyl or ethyl, with methyl being preferred.

Also preferred on account of their biological activity are compounds of formula I wherein $R_1$, $R_2$ and $R_5$ are methyl.

Halogen in the definition of $R_3$ and $R_4$ denotes fluorine, chlorine, bromine or iodine, with fluorine or chlorine being preferred.

Alkyl and alkoxy groups $R_1$ to $R_5$ can be in straight chain or branched chain configuration. Examples of such groups are: methyl, methoxy, ethyl, ethoxy, propyl, propoxy, isopropyl, isopropoxy, n-butyl, n-butoxy, isobutyl and the like.

The compounds of formula I can be prepared by
(a) reacting a compound of formula II

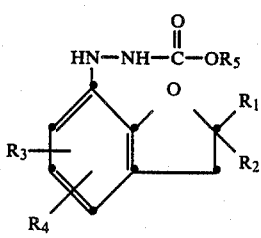

with fluorophosgene ($COF_2$) or monofluorophosgene (COClF), or
(b) reacting a compound of formula III

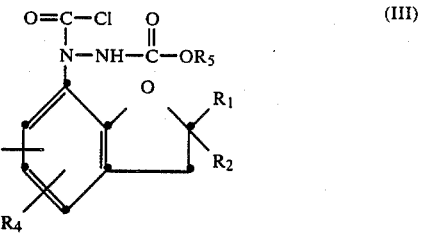

with a compound that replaces chlorine by fluorine, in which formulae II and III above the substituents $R_1$ to $R_5$ are as previously defined.

Process (a) for obtaining the compounds of formula I conforms to the already known reaction of substituted hydrazinecarboxylic acid esters with phosgene to form corresponding 2-chlorocarbonyl derivatives (q.v. European patent specification No. 0 067 471, Japanese patent specification Nos. J5 9222 490, J5 8222 085 and J5 8222 083. Fluorophosgenations are known per se from J. Chem. Soc. 1948, 2183.

The process is carried out at a reaction temperature in the range from −10° to +120° C., normally from 20° to 80° C., under normal or elevated pressure, and preferably in an inert solvent or diluent. Examples of suitable solvents and diluents are: ether and ethereal compounds such as diethyl ether, dipropyl ether, dioxane, dimethoxyethane and tetrahydrofuran; aliphatic, aromatic and halogenated hydrocarbons, preferably benzene, toluene, xylenes, chloroform and chlorobenzene; as well as esters, e.g. ethyl acetate.

In process (b), chlorocarbonyl compounds of formula III are converted into the corresponding compounds of formula I by reaction with e.g. alkali metal fluorides in suitable solvents, with the optional addition of crown compounds or phase transfer catalysts, or by reaction with anhydrous hydrofluoric acid, antimony fluoride or another suitable reagent that replaces chlorine by fluorine (q.v. Angew. Chemie 89, 797, 1977).

The starting substituted hydrazinecarboxylic acid esters of formula II and 2-chlorocarbonylhydrazinecarboxylic acid esters of formula III are known or can be obtained by methods analogous to known ones. Thus the hydrazinecarboxylic acid esters of formula II can be obtained by reacting unsubstituted or substituted 2,3-dihydrobenzofuran-7-ylhydrazines with an appropriate chloroformate (q.v. European patent application No. 0 048 040). The 2-chlorocarbonylhydrazinecarboxylic acid esters of formula III can be obtained in accordance with the literature cited in connection with process a).

Pesticidally, especially insecticidally, active esters of 2-(2,3-dihydrobenzofuran-7-yl)hydrazinecarboxylic acid are disclosed in U.S. Pat. No. 4 467 104, European patent specification No. 0 067 471 and European patent application No. 0 048 040. The compounds of formula I of the present invention differ structurally from these known compounds in that they contain a 2-fluorocarbonylhydrazine group.

Surprisingly, it has now been found that the compounds of formula I exhibit superior activity as pesticides, while being well tolerated by plants and having low mammalian toxicity to warm-blooded animals. The compounds of formula I are especially suitable for controlling pests that attack plants and animals, in particular for eradicating sucking insects.

In particular, the compounds of formula I are suitable for controlling insects of the orders: Lepidoptera, Coleoptera, Homoptera, Heteroptera, Diptera, Thysanoptera, Orthoptera, Anoplura, Siphonaptera, Mallophaga, Thysanura, Isoptera, Psocoptera and Hymenoptera, as well as representatives of the order Acarina.

The good pesticidal activity of the compounds of the invention corresponds to a mortality of at least 50-60% of the above pests.

The compounds of formula I are suitable for controlling in particular plant-destructive insects, especially plant-destructive insects in ornamentals and crops of useful plants, above all in cotton, vegetable, rice and fruit crops. In this connection, particular attention is drawn to the fact that the compounds of formula I have both a strongly pronounced systemic and, in particular, contact action against sucking insects, especially against sucking insects of the Aphididae family (e.g. against *Aphis fabae, Aphis craccivora* and *Myzus persicae*), which can only be controlled with difficulty using known pesticides.

The compounds of formula I also exhibit good activity against larval insect stages and nymphs, especially of noxious sucking insects. In particular, the compounds of formula I can be used with great success to control plant-destructive cicadas, especially in rice crops. The compounds of formula I are also suitable for controlling ectoparasites, e.g. *Lucilia sericata,* and ticks on domestic animals and productive livestock, e.g. by treating animals, barns, stables and the like, and pastures.

The activity of the compounds of formula I and of the compositions containing them can be substantially broadened and adapted to prevailing circumstances by addition of other insecticides and/or acaricides. Examples of suitable additives include: organophosphorus compounds, nitrophenols and derivatives thereof, formamidines, ureas, carbamates, pyrethroids, chlorinated hydrocarbons, and Bacillus thuringiensis preparations.

The compounds of formula I are used in unmodified form, or preferably together with the adjuvants conventionally employed in the art of formulation, and are therefore formulated in known manner to emulsifiable concentrates, directly sprayable or dilutable solutions, dilute emulsions, wettable powders, soluble powders, dusts, granulates, and also encapsulations in e.g. polymer substances. As with the compositions, the methods of applicartion such as spraying, atomising, dusting, scattering or pouring, are chosen in accordance with the intended objectives and the prevailing circumstances.

The formulations, i.e. the compositions, preparations or mixtures containing the compound (active ingredient) of formula I or combinations thereof with other insecticides or acaricides, and, where appropriate, a solid or liquid adjuvant, are prepared in known manner, e.g. by homogeneously mixing and/or grinding the active ingredients with extenders, e.g. solvents, solid carriers and, in some cases, surface-active compounds (surfactants).

Suitable solvents are: aromatic hydrocarbons, preferably the fractions containing 8 to 12 carbon atoms, e.g. xylene mixtures or substituted naphthalenes, phthalates such as dibutyl phthalate or dioctyl phthalate, aliphatic hydrocarbons such as cyclohexane or paraffins, alcohols and glycols and their ethers and esters, such as ethanol, ethylene glycol, ethylene glycol monomethyl or monoethyl ether, ketones such as cyclohexanone, strongly polar solvents such as N-methyl-2-pyrrolidone, dimethyl sulfoxide or dimethylformamide, as well as vegetable oils or epoxidised vegetable oils such as epoxidised coconut oil or soybean oil; or water.

The solid carriers used e.g. for dusts and dispersible powders are normally natural mineral fillers such as calcite, talcum, kaolin, montmorillonite or attapulgite. To improve the physical properties it is also possible to add highly dispersed silicic acids or highly dispersed absorbent polymers. Suitable granulated adsorptive carriers are porous types, for example pumice, broken brick, sepiolite or bentonite; and suitable nonsorbent carriers are materials such as calcite or sand. In addition, a great number of pregranulated materials of inorganic or organic nature can be used, e.g. especially dolomite or pulverised plant residues.

Depending on the nature of the compound of formula I to be formulated, or of combinations thereof with other insecticides or acaricides, suitable surface-active compounds are non-ionic, cationic and/or anionic surfactants having good emulsifying, dispersing and wetting properties. The term "surfactants" will also be understood as comprising mixtures of surfactants.

Suitable anionic surfactants can be both water-soluble soaps and water-soluble synthetic surface-active compounds.

Suitable soaps are the alkali metal salts, alkaline earth metal salts or unsubstituted or substituted ammonium salts of higher fatty acids ($C_{10}$–$C_{22}$), e.g. the sodium or potassium salts of oleic or stearic acid, or of natural fatty acid mixtures which can be obtained, e.g. from coconut oil or tallow oil. Further suitable surfactants are also the fatty acid methyltaurin salts as well as modified and unmodified phospholipids.

More frequently, however, so-called synthetic surfactants are used, especially fatty sulfonates, fatty sulfates, sulfonated benzimidazole derivatives or alkylarylsulfonates.

The fatty sulfonates or sulfates are usually in the form of alkali metal salts, alkaline earth metal salts or unsubstituted or substituted ammonium salts and generally contain a $C_8$–$C_{22}$alkyl radical which also includes the alkyl moiety of acyl radicals, e.g. the sodium or calcium salt of lignosulfonic acid, or dodecylsulfate, or of a mixture of fatty alcohol sulfates obtained from natural fatty acids. These compounds also comprise the salts of sulfated and sulfonated fatty alcohol/ethylene oxide adducts. The sulfonated benzimidazole derivatives preferably contain 2 sulfonic acid groups and one fatty acid radical containing about 8 to 22 carbon atoms. Examples of alkylarylsulfonates are the sodium, calcium or triethanolamine salts of dodecylbenzenesulfonic acid, dibutylnaphthalenesulfonic acid, or of a condensate of naphthalenesulfonic acid and formaldehyde. Also suitable are corresponding phosphates, e.g. salts of the phosphoric acid ester of an adduct of p-nonylphenol with 4 to 14 moles of ethylene oxide.

Non-ionic surfactants are preferably polyglycol ether derivatives of aliphatic or cycloaliphatic alcohols, or saturated or unsaturated fatty acids and alkylphenols, said derivatives containing 3 to 30 glycol ether groups and 8 to 20 carbon atoms in the (aliphatic) hydrocarbon moiety and 6 to 18 carbon atoms in the alkyl moiety of the alkylphenols.

Further suitable non-ionic surfactants are the water-soluble adducts of polyethylene oxide with polypropylene glycol, ethylenediaminopolypropylene glycol and alkylpolypropylene glycol containing 1 to 10 carbon atoms in the alkyl chain, which adducts contain 20 to 250 ethylene glycol ether groups and 10 to 100 propylene glycol ether groups. These compounds usually contain 1 to 5 ethylene glycol units per propylene glycol unit.

Representative examples of non-ionic surfactants are nonylphenolpolyethoxyethanols, castor oil polyglycol ethers, polypropylene/polyethylene oxide adducts, tributylphenoxypolyethoxyethanol, polyethylene glycol and octylphenoxypolyethoxyethanol. Fatty acid esters of polyoxyethylene sorbitan, e.g. polyoxyethylene sorbitan trioleate, are also suitable non-ionic surfactants.

Cationic surfactants are preferably quaternary ammonium salts which contain, as N-substituent, at least one $C_8$–$C_{22}$alkyl radical and, as further substituents, unsubstituted or halogenated lower alkyl, benzyl or hydroxy-lower alkyl radicals. The salts are preferably in the form of halides, methylsulfates or ethylsulfates, e.g. stearyltrimethylammonium chloride or benzyldi(2-chloroethyl)ethylammonium bromide.

The surfactants customarily employed in the art of formulation are described e.g. in "McCutcheon's Detergents and Emulsifiers Annual", MC Publishing Corp., Ridgewood, N.J., 1979; Dr. Helmut Stache, "Tensid Taschenbuch" (Handbook of Surfactants), Carl Hanser Verlag, Munich/Vienna, 1981.

The pesticidal compositions of this invention normally contain 0.1 to 99%, preferably 0.1 to 95%, of a compound of formula I or combination thereof with other insecticides or acaricides, 1 to 99.9% of a solid or liquid adjuvant, and 0 to 25%, preferably 0.1 to 20%, of a surfactant.

Whereas commercial products are preferably formulated as concentrates, the end user will normally employ dilute formulations of substantially lower concentration.

The compositions may also contain further ingredients, such as stabilisers, antifoams, viscosity regulators, binders, tackifiers as well as fertilisers or other active ingredients to obtain special effects.

EXAMPLE 1

Preparation of 2-(2-fluorocarbonyl)-2-(2,3-dihydro-2,2-dimethylbenzofuran-7-yl)hydrazinecarboxylic acid methyl ester (compound 1)

5 g of 2-(2,3-dihydro-2,2-dimethylbenzofuran-7-yl)hydrazinecarboxylic acid methyl ester are dispersed in 50 ml of toluene in an autoclave and to this mixture are added 10 g of fluorophosgene under pressure. The mixture is stirred at room temperature for 24 hours in the autoclave and then excess gas is expelled with air. The reaction solution is subsequently washed three times with water and once with 5% sodium bicarbonate solution, dried over sodium sulfate, and the solvent is removed under vacuum. The crystalline residue is recrystallised from tetrachloromethane.

The resultant compound 1 of formula

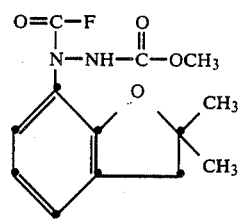

has a melting point of 104°–106° C.

The following compounds of formula I can be obtained by the procedure described in this Example:

| Compound | $R_1$ | $R_2$ | $R_3$ | $R_4$ | $R_5$ | m.p. C.° |
|---|---|---|---|---|---|---|
| 1 | —$CH_3$ | —$CH_3$ | H | H | —$CH_3$ | 104–106° |
| 2 | —$CH_3$ | —$CH_3$ | 5-$CH_3$ | H | —$CH_3$ | 107–110° |
| 3 | —$CH_3$ | —$CH_3$ | H | 4-$CH_3$ | —$CH_3$ | 121–123° |
| 4 | —$CH_3$ | —$CH_3$ | H | H | —$C_2H_5$ | 101.5–102.5° |
| 5 | —$CH_3$ | —$CH_3$ | H | 4-$CH_3$ | —$C_2H_5$ | 95–98° |
| 6 | —$CH_3$ | —$CH_3$ | H | H | —$C_3H_7$(n) | |
| 7 | —$CH_3$ | —$CH_3$ | H | H | —$C_3H_7$(i) | |
| 8 | —$CH_3$ | —$CH_3$ | 5-$CH_3$ | H | —$C_2H_5$ | |
| 9 | —$CH_3$ | —$CH_3$ | H | 4-$CH_3$ | —$C_3H_7$(i) | |
| 10 | —$CH_3$ | —$CH_3$ | 5-$CH_3$ | 4-$CH_3$ | —$CH_3$ | |

EXAMPLE 2

Formulations for active ingredients of formula I according to Example 1 or combinations thereof with other insecticides or acaricides (throughout, percentages are by weight)

| 1. Wettable powders | (a) | (b) | (c) |
|---|---|---|---|
| active ingredient or active ingredient combination | 25% | 50% | 75% |
| sodium lignosulfonate | 5% | 5% | — |
| sodium laurylsulfate | 3% | — | 5% |
| sodium diisobutylnaphthalenesulfonate | — | 6% | 10% |
| octylphenol polyethylene glycol ether (7–8 moles of ethylene oxide) | — | 2% | — |
| highly dispersed silicic acid | 5% | 10% | 10% |
| kaolin | 62% | 27% | — |

The active ingredient or active ingredient combination is thoroughly mixed with the adjuvants and the mixture is thoroughly ground in a suitable mill, affording wettable powders which can be diluted with 16ter to give suspensions of any desirable concentration.

| 2. Emulsifiable concentrate | |
|---|---|
| active ingredient or active ingredient combination | 10% |
| octylphenol polyethylene glycol ether (4–5 moles of ethylene oxide) | 3% |
| calcium dodecylbenzenesulfonate | 3% |
| castor oil polyglycol ether (36 moles of ethylene oxide) | 4% |
| cyclohexanone | 30% |
| xylene mixture | 50% |

Emulsions of any required concentration can be obtained from this concentrate by dilution with water.

| 3. Dusts | (a) | (b) |
|---|---|---|
| active ingredient or active ingredient combination | 5% | 8% |

| 3. Dusts | (a) | (b) |
|---|---|---|
| talcum | 95% | — |
| kaolin | — | 92% |

Ready for use dusts are obtained by mixing the active ingredient or active ingredient combination with the carrier, and grinding the mixture in a suitable mill.

| 4. Extruder granulate | |
|---|---|
| active ingredient or active ingredient combination | 10% |
| sodium lignosulfonate | 2% |
| carboxymethylcellulose | 1% |
| kaolin | 87% |

The active ingredient or active ingredient combination is mixed and ground with the adjuvants, and the mixture is subsequently moistened with water. The mixture is extruded, granulated and then dried in a stream of air.

| 5. Coated granulate | |
|---|---|
| active ingredient or active ingredient combination | 3% |
| polyethylene glycol (mol. wt. 200) | 3% |
| kaolin | 94% |

The finely ground active ingredient or active ingredient combination is uniformly applied, in a mixer, to the kaolin moistened with polyethylene glycol. Non-dusty coated granulates are obtained in this manner.

| 6. Suspension concentrate | |
|---|---|
| active ingredient or active ingredient combination | 40% |
| ethylene glycol | 10% |
| nonylphenol polyethylene glycol ether (15 moles of ethylene oxide) | 6% |
| sodium lignosulfonate | 10% |
| carboxymethylcellulose | 1% |
| 37% aqueous formaldehyde solution | 0.2% |
| silicone oil in the form of a 75% aqueous emulsion | 0.8% |
| water | 32% |

The finely ground active ingredient or active ingredient combination is intimately mixed with the adjuvants, giving a suspension concentrate from which suspensions of any desired concentration can be obtained by dilution with water.

EXAMPLE 3

Action against *Musca domestica*

50 g of freshly prepared CMSA nutrient substrate for maggots are charged into each of a number of beakers. A specific amount of an acetonic solution containing 1% by weight of the respective test compound is pipetted onto the nutrient substrate present in the beakers to give an active ingredient concentration of 400 ppm. The substrate is then thoroughly mixed and the acetone subsequently allowed to evaporate over a period of at least 20 hours.

Then 25 one-day-old maggots of *Musca domestica* are put into each of the beakers containing the treated nutrient substrate for testing with each active ingredient at the given concentration. After the maggots have pupated, the pupae are separated from the substrate by flushing them out with water and then deposited in containers closed with a perforated top.

Each batch of flushed out pupae is counted to determine the toxic effect of the test compound on the maggot development. A count is then made after 10 days of the number of flies which have hatched out of the pupae.

Compounds of formula I according to Example 1 are very effective in this test.

EXAMPLE 4

Action against *Lucilia sericata* (larvae) 1 ml of an aqueous formulation containing 0.5% of test compound is added at 50° C. to 9 ml of a culture medium. Then about 30 freshly hatched *Lucilia sericata* larvae are added to the culture medium, and the insecticidal action is determined after 48 and 96 hours by evaluating the mortality rate.

In this test, compounds of formula I according to Example 1 are very effective against *Lucilia sericata*.

EXAMPLE 5

Action against *Aëdes aegypti* (larvae)

A concentration of 200 ppm is obtained by pipetting a specific amount of a 0.1% solution of the test compound in acetone onto the surface of 150 ml of water in a beaker. After the acetone has evaporated, 30 to 40 two-day old larvae of *Aedes aegypti* are put into the beaker containing the test compound. Mortality counts are made after 2 and 7 days.

Compounds of formula I according to Example 1 are very effective in this test.

EXAMPLE 6

Contact action against *Aphis craccivora*

Before the start of the test, 4- to 5-day old bean plants (*Vicia faba*) reared in pots are each populated with about 200 insects of the species *Aphis craccivora*. The treated plants are sprayed direct to drip point 24 hours later with an aqueous formulation containing the test compound. Two plants are used for each test compound at its given concentration. A mortality count is made after 24 and 72 hours respectively. The test is carried out at 21°-22° C. and at a relative humidity of about 55%.

In the test, compound 1 according to Example 1 effects 80 to 100% kill at 1 ppm.

EXAMPLE 7

Systemic action against *Aphis craccivora*

Bean plants which have grown roots are transplanted into pots containing 600 ccm of soil. Then 50 ml of a formulation (prepared from a 25% wettable powder) of the test compound in a concentration of 800 ppm are poured direct onto the soil in the pots.

After 24 hours the growing parts of the plants are populated with aphids of the species *Aphis craccivora* and a plastic cylinder is then slipped over the plants to protect the aphids from any possible contact with the test substance either direct or via the gas phase.

A mortality count is made 48 and 72 hours respectively after the start of the test. Two plants, each in a separated pot, are used for each test substance at its given concentration. The test is carried out at 25° C. and about 70% relative humidity.

Compounds of formula I according to Example 1 are very effective in this test.

EXAMPLE 8

Contact action against *Myzus persicae*

4- to 5-day old bean plants (*Vicia faba*) which have been reared in water are each populated with about 200 aphids of the species *Myzus persicae* before the start of the test. The treated plants are sprayed direct to drip point 24 hours later with an aqueous suspension containing the test compound in a concentration of up to 200 ppm. Two plants are used for each compound at its given concentration. A mortality count is made 24 hours after application. The test is carried out at 20°-22° C. and about 55% relative humidity.

In this test, compound 1 according to Example 1 effects 80 to 100% kill at the indicated concentrations.

EXAMPLE 9

Systemic action against *Myzus persicae*

Cabbage plants which have grown roots are transplanted in the 4- to 5-leaf stage into pots containing 60 ccm of soil. Then 50 ml of an aqueous formulation (prepared from a 25% wettable powder) of the test compound in a concentration of 400 ppm are poured direct onto the soil.

After 24 hours the growing parts of the plants are populated with aphids of the species *Myzus persicae* and plastic cylinders are then slipped over the plants to protect the aphids for any possible contact with the test substance either direct or via the gas phase.

The evaluation of percentage mortality is made 48 hours after the start of the test. Two plants, each in a separate pot, are used for each test substance at its given concentration. The test is carried out at about 25° C. and 60% relative humidity.

Compounds of formula I according to Example 1 are very effective in this test.

EXAMPLE 10

Leaf penetration action against *Aphis craccivora*

A small shoot of *Vicia faba*, which is highly infested with aphids of the species *Aphis craccivora*, is placed in each of a number of 8 cm high plastic beakers (diameter about 6 cm). Each beaker is covered with a plastic lid having a punched opening of 2 cm diameter in the centre. A leaf of a *Vicia faba*-plant is then placed over the opening in the lid without separating this leaf from the potted plant. The leaf is then fixed on the beaker with a second punched lid above the opening of the first lid. From underneath, i.e. through the opening of the first lid, the aphids in the beaker then infect the leaf of the plant used as bait. An aqueous formulation of the test compound is then applied in a concentration of 400 ppm uniformly with a brush to the top side of the leaf. An investigation is then made to determine whether the test substance applied to the top side of the leaf of the plant used as bait has diffused in sufficient amount through the leaf to its underside to kill aphids sucking thereon.

The test is carried out at about 20° C. and 60% relative humidity. The evaluation of percentage mortality is made 48 hours after application of the test compound.

Compounds of formula I according to Example 1 are very effective in this test.

EXAMPLE 11

Stomach toxicant action against *Laodelphax striatellus* and *Nilaparvata lugens* (nymphs)

The test is carried out with growing plants. For this purpose 4 rice plants (thickness of stem 8 mm) about 20 cm in height are planted into each of a rubber of pots (diameter 8 cm). The plants in each pot are sprayed on a rotary table with 100 ml of an acetonic solution containing 800 ppm of the respective test compound. After the spray coating has dried, each plant is populated with 20 nymphs of the test organisms in the third stage. To prevent the cicadas from escaping, a glass cylinder open at both ends is slipped over each of the plants and sealed with a gauze top. The nymphs are kept for 10 days on the treated plant until the next development stage has been reached. Evaluation of percentage mortality is made 1, 4 and 8 days after treatment.

Compounds of formula I according to Example 1 are very effective in this test.

EXAMPLE 12

Insecticidal action against feeding insects

Cotton plants about 25 cm high, in pots, are sprayed with aqueous emulsions which contain the test compound in a concentrations of 400 ppm. After the spray coating has dried, the cotton plants are populated with *Spodoptera littoralis* and *Heliothis virescens* larvae in the $L_3$-stage. The test is carried out at 24° C. and about 60% relative humidity. The percentage mortality of the test insects is determined after 120 hours by making a comparison with untreated control insects.

Compound 1 of Example 1 effects 80-100% kill of spodoptera larvae in this test.

EXAMPLE 13

Ovicidal action against *Heliothis virescens*

Correponding amounts of a wettable powder formulation containing 25% by weight of the test compound are mixed with sufficient water to produce an aqueous emulsion with an active ingredient concentration of 800 ppm. One day-old egg deposits of Heliothis on cellophane are immersed in these emulsions for 3 minutes and then collected by suction on round filters. The treated deposits are placed in petri dishes and kept in the dark. The hatching rate in comparison with untreated controls is determined after 6 to 8 days. For further evaluation, the minimum inhibitory concentration necessary to effect 80-100% kill of the eggs is determined.

In this test the compounds of formula I according to Example 1 exhibit good ovicidal action.

EXAMPLE 14

Action against soil insects (*Diabrotica balteata*)

350 ml of soil (consisting of 95 vol.% of sand and 5 vol.% of peat) are mixed with 150 ml of each of a number of aqueous emulsion formulations which contain the test compound in a concentration of 400 ppm. Plastic beakers with a diameter of about 10 cm at the top are then partly filled with the treated soil. Ten $L_3$ larvae of *Diabrotica balteata* are put into each beaker, then 4 maize seedlings are planted and the beaker is filled up with soil. The beakers are sealed with plastic sheeting and kept at about 22° C. Ten days later then soil in the beakers is sieved and a mortality count of the remaining larvae is made.

Compounds of formula I according to Example 1 are very effective in this test.

EXAMPLE 15

Systemic insecticidal action against *Nilaparvata lugens*

Rice plants are treated with 5 ml of a solution containing 400 ppm of test compound and are each populated with 20 *Nilaparvata* nymphs after 1, 2 and 3 weeks. A mortality count is made in each case 6 days after infestation.

Compounds of formula I according to Example 1 are very effective in this test.

EXAMPLE 16

Action against *Nephotettix cincticeps* (nymphs)

The test is carried out with growing plants. The plants, about 20 days old and about 15 cm in height, are planted in pots having a diameter of 5.5 cm.

The plants are sprayed on a rotary table with 100 ml of an acetonic solution containing 400 ppm of test compound. After the spray coating has dried, the plants are populated with 20 nymphs of the test insects in the second or third stage. To prevent the cicadas from escaping, a plexiglass cylinder is slipped over each plant and sealed with a gauze cover. The nymphs are kept for 5 days on each treated plant, to which the solution of the test compound must be applied again at least once. The test is carried out at a temperature of c. 23° C. at 55% relative humidity and over an exposure period of 16 hours.

Compounds 1 and 3 according to Example 1 are very effective in tis test.

EXAMPLE 17

Action against *Aonidiella aurantii*

A solution of the test compound having a concentration of 100 ppm in a 1:1 mixture of acetone/water is prepared. Potato tubers which were infected 14 days previously with a population of *Aonidiella aurantii* (California red scales) are immersed in this solution for a short time. After the infected potato tubers have dried, they are kept for 6 to 8 weeks at 22°-24° C. in a dish covered with a sieve top. Evaluation of percentage mortality and any juvenile development and oviposition is made after this time.

Compounds 1 and 3 of Example 1 are very effective in this test.

What is claimed is:

1. A compound of formula I

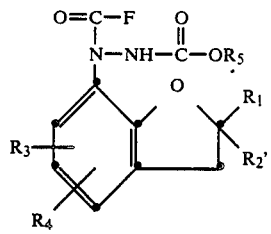

wherein
$R_1$ and $R_2$ are each independently of the other hydrogen or $C_1$-$C_3$alkyl,
$R_3$ and $R_4$ are each independently of the other hydrogen, halogen, $C_1$-$C_4$alkyl or $C_1$-$C_4$-alkoxy, and
$R_5$ is $C_1$-$C_4$alkyl.

2. A compound of formula I according to claim 1, wherein $R_1$, $R_2$, $R_3$ and $R_4$ are each independently hydrogen or methyl and $R_5$ is methyl or ethyl.

3. A compound of formula I according to claim 1, wherein $R_1$, $R_2$, $R_3$ and $R_4$ are each independently hydrogen or methyl and $R_5$ is methyl.

4. A compound of formula I according to claim 1, wherein $R_1$, $R_2$ and $R_5$ are methyl and $R_3$ and $R_4$ are each independently hydrogen or methyl.

5. A compound according to claim 1 of formula

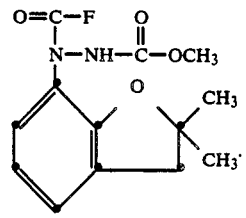

6. A compound according to claim 1 of formula

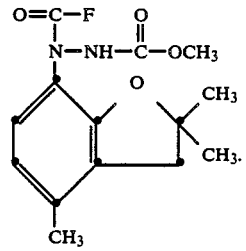

7. A pesticidal composition which comprises, as active component, a pesticidally effective amount of a compound as claimed in claim 1, together with a suitable carrier or other adjuvant.

8. A method of controlling insects and representatives of the order Acarina, which comprises contacting or treating said pests, their different development stages and/or the locus thereof, with a pesticidally effective amount of a compound of formula I as claimed in claim 1, or with a composition that contains a pesticidally effective amount of such a compound, together with adjuvants and carriers.

* * * * *